United States Patent
Osorio et al.

(10) Patent No.: US 9,462,958 B2
(45) Date of Patent: Oct. 11, 2016

(54) METHOD AND SYSTEM FOR USING TRI-MODAL SENSOR

(71) Applicant: Flint Hills Scientific, L.L.C., Lawrence, KS (US)

(72) Inventors: Ivan Osorio, Leawood, KS (US); Nachappa Gopalsami, Argonne, IL (US); Apostolos C. Raptis, Argonne, IL (US); Stanislav Kulikov, Sarov (RU)

(73) Assignee: FLINT HILLS SCIENTIFIC, LLC, Lawrence, KS (US)

( * ) Notice: Subject to any disclaimer, the term of this patent is extended or adjusted under 35 U.S.C. 154(b) by 349 days.

(21) Appl. No.: 14/148,610

(22) Filed: Jan. 6, 2014

(65) Prior Publication Data

US 2014/0275830 A1 Sep. 18, 2014

Related U.S. Application Data

(60) Provisional application No. 61/800,728, filed on Mar. 15, 2013.

(51) Int. Cl.
| | |
|---|---|
| *A61B 5/0476* | (2006.01) |
| *A61B 5/021* | (2006.01) |
| *A61B 5/00* | (2006.01) |
| *A61B 5/01* | (2006.01) |
| *A61B 5/03* | (2006.01) |
| *A61B 5/0215* | (2006.01) |
| *A61B 5/024* | (2006.01) |
| *A61B 5/08* | (2006.01) |

(52) U.S. Cl.
CPC ........... *A61B 5/0476* (2013.01); *A61B 5/0031* (2013.01); *A61B 5/031* (2013.01); *A61B 5/032* (2013.01); *A61B 5/6868* (2013.01); *A61B 5/01* (2013.01); *A61B 5/0215* (2013.01); *A61B 5/02438* (2013.01); *A61B 5/0816* (2013.01); *A61B 5/4836* (2013.01); *A61B 5/6869* (2013.01); *A61B 5/6876* (2013.01)

(58) Field of Classification Search
None
See application file for complete search history.

(56) References Cited

U.S. PATENT DOCUMENTS

| | | | | |
|---|---|---|---|---|
| 7,212,110 | B1 * | 5/2007 | Martin | A61N 1/3727 128/903 |
| 7,697,972 | B2 * | 4/2010 | Verard | A61B 1/00071 600/407 |
| 2006/0173522 | A1 * | 8/2006 | Osorio | A61B 5/6864 607/116 |
| 2011/0172659 | A1 * | 7/2011 | Brannan | A61B 18/1815 606/42 |
| 2012/0035583 | A1 * | 2/2012 | Sepkuty | A61B 5/4094 604/503 |

FOREIGN PATENT DOCUMENTS

WO  WO2014/071079  * 5/2014  ............... A61B 5/04

* cited by examiner

*Primary Examiner* — Brian T Gedeon
(74) *Attorney, Agent, or Firm* — Williams Morgan, P.C.

(57) ABSTRACT

In some embodiments, the present disclosure relates to a medical device system, comprising: a medical device capable of receiving a plurality of body signal types, wherein the body signal types comprise an electrical body signal, a temperature body signal, or a pressure body signal; and an electrode operatively coupled to the medical device, the electrode capable of sensing a plurality of body signal types, wherein the body signal types comprise an electrical body signal, a temperature body signal, or a pressure body signal; the electrode comprising: an electrical sensor; a temperature sensor; and a pressure sensor.

23 Claims, 12 Drawing Sheets

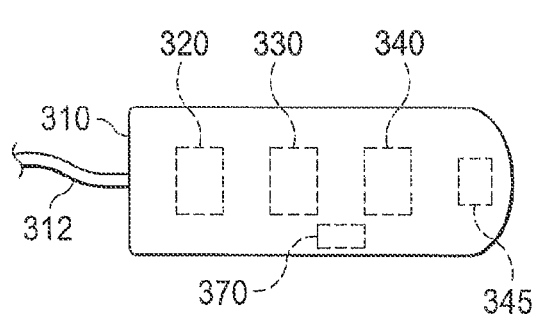
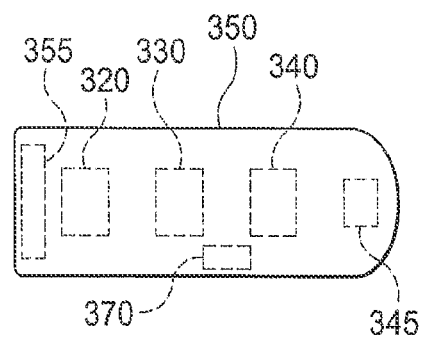
FIG. 3A          FIG. 3B
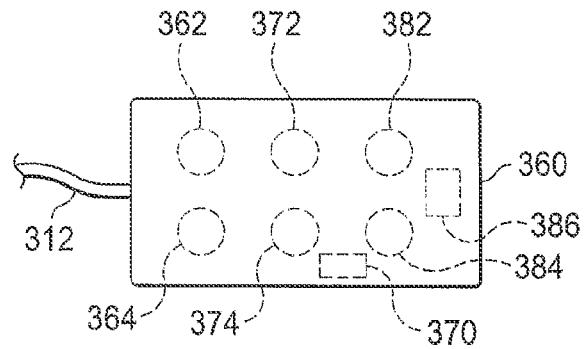
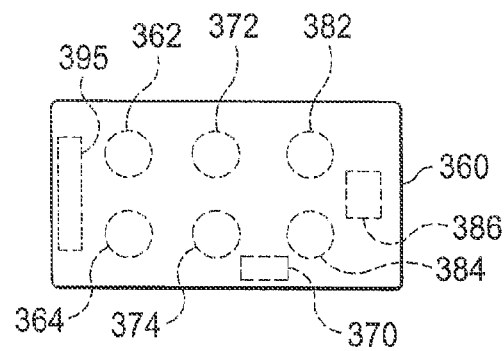
FIG. 3C          FIG. 3D
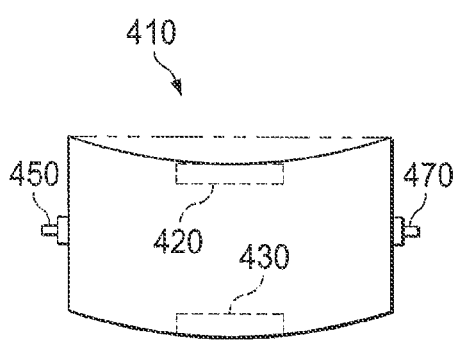
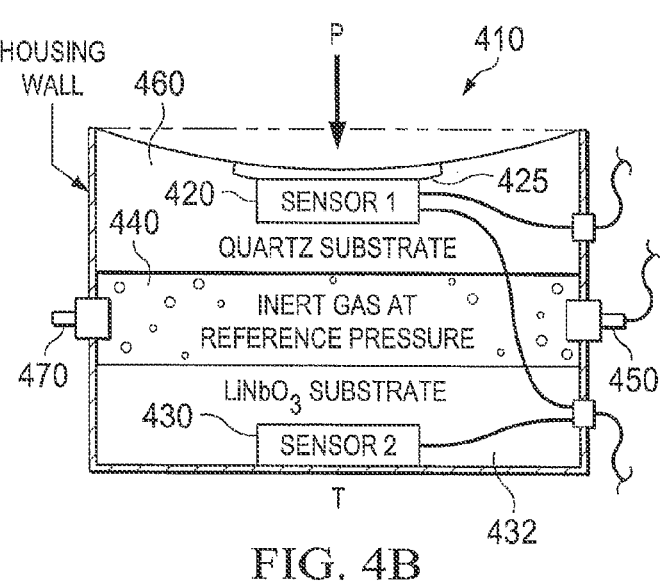
FIG. 4A          FIG. 4B

METHOD AND SYSTEM FOR USING TRI-MODAL SENSOR

BACKGROUND OF THE INVENTION

This application claims priority to U.S. Provisional Application Ser. No. 61/800,728 filed Mar. 15, 2013.

FIELD OF THE INVENTION

This disclosure relates to medical device systems and methods capable of detecting body signals.

SUMMARY OF THE INVENTION

In some embodiments, the present disclosure relates to an apparatus for sensing a body signal of a patient, comprising: a sensor capable of sensing a plurality of body signal types, wherein the body signal types comprise an electrical body signal, a temperature body signal, and a pressure body signal; the probe comprising: an electrical sensor; a temperature sensor; and a pressure sensor.

In some embodiments, the present disclosure relates to a medical device system comprising: a probe comprising an electrical sensor capable of sensing an electrical body signal, a temperature sensor capable of sensing a body temperature signal, and a pressure sensor capable of sensing a body pressure signal; and a medical device capable of receiving said electrical body signal, said body temperature and said body pressure signal from said probe.

In some embodiments, the present disclosure relates to a medical device, comprising: a probe comprising an electrical sensor capable of sensing an electrical body signal, a temperature sensor capable of sensing a temperature body signal, and a pressure sensor capable of sensing a pressure body signal; and a functional mapping unit to provide a functional mapping of a patient's brain.

DESCRIPTION OF THE DRAWINGS

The disclosure may be understood by reference to the following description taken in conjunction with the accompanying drawings, in which like reference numerals identify like elements, and in which:

FIG. 3A shows a stylized representation of a tri-modal sensor, in accordance with one embodiment of the present disclosure.

FIG. 3B shows a stylized representation of a wireless tri-modal sensor, in accordance with one embodiment of the present disclosure.

FIG. 3C shows a stylized representation of a tri-modal sensor comprising a matrix, in accordance with another embodiment of the present disclosure.

FIG. 3D shows a stylized representation of a wireless tri-modal sensor comprising a matrix, in accordance with another embodiment of the present disclosure.

FIG. 4A shows a stylized diagram of a tri-modal sensor, in accordance with some embodiments of the present disclosure.

FIG. 4B shows a stylized cross-section representation of the tri-modal sensor of FIG. 4A, in accordance with some embodiments of the present disclosure.

Figure 1:
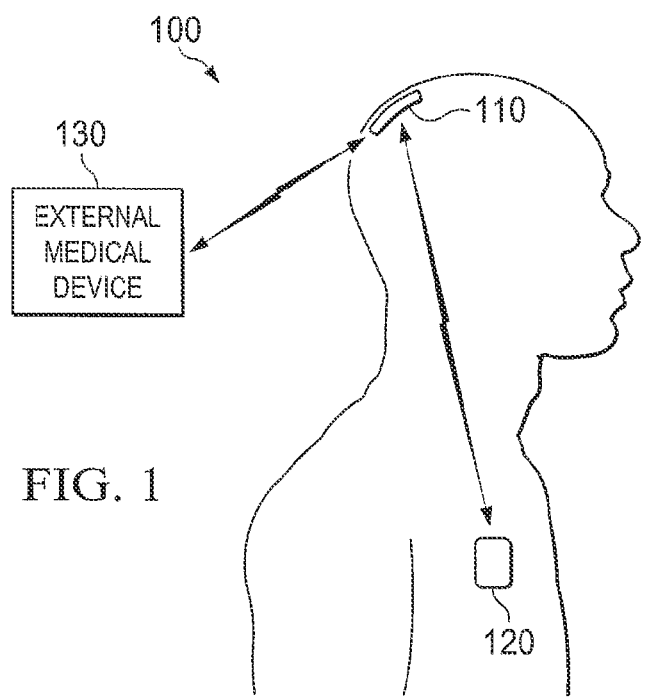
FIG. 1 shows a schematic diagram of a medical device system incorporating a tri-modal sensor, according to some embodiments of the present disclosure.

The disclosure is susceptible to various modifications and alternative forms. Specific embodiments thereof have been shown by way of example in the drawings and are herein described in detail. It should be understood, however, that the description of specific embodiments is not intended to limit the disclosure to the particular forms disclosed, and the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

More information regarding detecting an epileptic event from cardiac data, as well as information regarding measures of central tendency that can be determined from time series of body data, may be found in other patent applications assigned to Flint Hills Scientific, L. L. C. or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding detecting an epileptic event from multiple body data types, and examples of such body data types, may be found in other patent applications assigned to Flint Hills Scientific, L. L. C. or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding the detection of brain or body activity using sensors implanted in proximity to the base of the skull may be found in other patent applications assigned to Flint Hills Scientific, L.L.C. or Cyberonics, Inc., such as, U.S. Ser. No. 13/678,339, filed Nov. 15, 2012. Additional information on body sensors for detecting or predicting seizures may be found in U.S. Pat. No. 8,165,682, filed Jul. 31, 2006. The patent application and patent identified in this paragraph are hereby incorporated herein by reference.

Embodiments of the present disclosure provide for using a sensor that comprises multiple sensing components or elements for acquiring body signals. Using a single sensor, three types or modalities of body signals may be acquired from a single body location as part of a single sensor probe or package. For example a tri-modal sensor, in accordance with some embodiments herein, may provide for detecting an electrical signal, a temperature signal, and a pressure signal at a predetermined body location. The detected signals may be provided to a medical device for detecting medical conditions or normal or abnormal events, and/or performing a responsive action in response to detecting such conditions or events. The responsive action may include providing a therapy, issuing a warning or a written or graphic report, and/or logging data including the detection time, type of event, body signals proximate in time to the detection, and/or the therapy or action provided in response to the detection. As used herein the terms sensor, probe, and package may be used interchangeable in some instances. More generally, a sensor refers to a component, probe, package or element that includes a structure to achieve a sensing function of a body signal. A probe may refer to an assembly containing multiple components or elements including one or more sensing elements. A package may similarly refer to an assembly that includes one or more sensing elements, and may include, for example, a housing or probe including sensing elements for one or more body signals.

Turning now to FIG. 1, a medical device system 100 for implementing a tri-modal sensor, in accordance with embodiments of the present disclosure, is illustrated. The system 100 may comprise a tri-modal sensor 110 that is implanted or externally coupled to the patient's body, and to one or more of an implantable medical device (IMD) 120 or external medical device (EMD) 130. The tri-modal sensor 110 may receive commands from, and provide sensed data/signals to, the IMD 120 or EMD 130.

Figure 7:
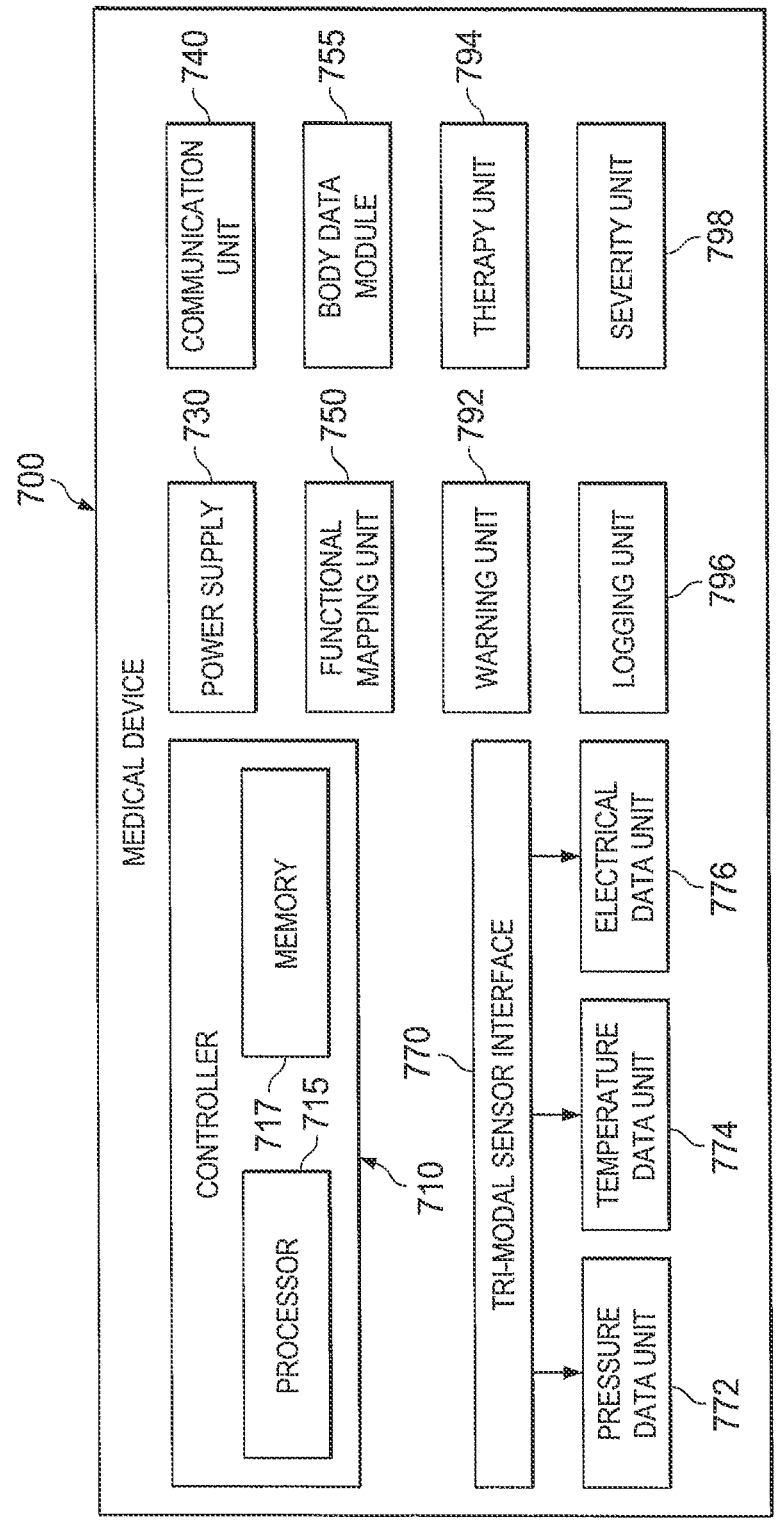
FIG. 7 shows a stylized depiction of a medical device capable of interfacing with a tri-modal sensor, in accordance with some embodiments of the present disclosure.

The system 100 may, in some embodiments, comprise an external medical device (EMD) 130. EMD 130 may wirelessly communicate with an implanted tri-modal sensor 110, or may communicate by wired or wireless connection if the tri-modal sensor is externally placed on the patient's body. In alternative embodiments (not shown), EMD 130 or IMD 120 may contain the tri-modal sensor 110. One or both of IMD 120 and EMD 130 may comprise a controller (e.g., controller 710 as shown in FIG. 7) capable of sending and receiving commands and data to and from the tri-modal sensor 110. In some embodiments, one or both of EMD 130 and IMD 120 may be capable of treating various disorders, such as epilepsy, depression, increased intracranial pressure, obesity, cardiac disease, respiratory disease, endocrine disease, etc. The IMD 120 and the EMD 130 may be capable of providing a therapy, including one or more of an electrical, chemical, thermal or mechanical therapy to the patient, and may also be capable of mapping organs such as the brain to localize certain cognitive (e.g., speech) or other functions (e.g., sensorimotor, visual).

In one embodiment, the tri-modal sensor 110 may be implanted into a head region for the simultaneous measurement of pressure, temperature and electrical activity of the brain. Brain function is customarily monitored via a single signal modality. At present, electrical neuronal activity (EEG) and imaging (SPECT, PET, fMRI) are the main tools to monitor the brain. Simultaneous acquisition of more than one signal type or modality (i.e., EEG and temperature) from the same site is not generally performed due at least in part to a lack of sensors capable of simultaneously acquiring various brain signal modalities from the same locus at the same time. Regional brain temperature and pressure, for example, are important indices of brain activity that are routinely ignored in assessing brain function.

Brain temperature and pressure provide useful information about the state of brain health and function. However, in the state of the art, it may be difficult to obtain brain temperature and pressure from EEG/ECoG, PET, SPECT, CT or MRI. Moreover, the temporal and or spatial resolution of temperature and pressure obtained from these tests may be limited, further diminishing their value for said tasks. Pressure within the skull/brain is usually measured only in certain pathological conditions manifesting with increased intracranial pressure, and then usually only from the ventricles (cerebrospinal fluid, CSF), not from the brain itself. Since the compressibility and elastic modulus of fluid is much smaller than that of actual brain tissue, CSF pressure measurements do not faithfully or accurately reflect changes in brain tissue pressure, a limitation that is most clearly demonstrated by normal pressure hydrocephalus (NPH). In NPH, with CSF pressure that is normal and brain function abnormal, ventriculo-peritoneal shunting leads to neurological improvement, suggesting that existing pressure measurements (using CSF as a proxy for the brain itself) fails to accurately indicate pressure changes indicative of neuropathology. Recording of brain temperature provides direct information about cerebral blood flow and metabolism and indirectly about electrical neuronal activity. Temperature and pressure both correlate with and influence brain activity.

Some embodiments herein may provide for substantially simultaneous/synchronous recording of brain temperature, pressure and electrical activity from the same locus. In one embodiment, a surface acoustic wave (SAW) sensor may be used in the tri-modal sensor 110 to detect temperature changes within the brain by implanting the tri-modal sensor into a seizure-prone area of the brain. Moreover, in addition to neurological applications, the sensor may be used for prolonged monitoring of systemic blood pressure and body temperature in ambulatory or hospitalized subjects.

The tri-modal sensor 110 may be configured to operate wirelessly and without a battery power source. In one embodiment, tri-modal sensor 110 may consist of two SAW sensors housed inside a cylindrical enclosure to measure temperature and pressure, while the metal housing itself is used as an electrical probe for neuronal activity. The two SAW sensors may be prepared of different piezoelectric materials so that one is sensitive to pressure only and the other to temperature only.

Simultaneous recording of three signal modalities (temperature, pressure and electrical activity) from the same site using a single probe would minimize brain trauma, because obtaining the same signals using current state of the art, would require three separate probes. Moreover, without a single device such as tri-modal sensor 110, these signals would not be recorded from the same locus/site. Embodiments disclosed herein allows recording of three different signal types from the same site using either a single probe or a single sensor, thus increasing information content.

Further, simultaneous recording of temperature, pressure, and electrical activity from the same brain site may provide equivalent information with some degree of redundancy, a feature that would decrease the probability of data loss or degradation due to noise contamination. For example, in the presence of intense power line (60 Hz) noise or during deep brain stimulation for seizure control, analysis of brain electrical activity is often very problematic due to degradation/distortion caused by the noise. Because the temperature and pressure signals are initially measured using acoustic waves, external electrical interference does not directly affect the data. Although the acoustic signals are transduced into electrical signals as part of the signal processing path in some embodiments, the risk of significant contamination by electrical noise is substantially reduced, and may be addressed by known signal processing techniques after the signals are transduced from the acoustical to the electrical domain. Further, using embodiments herein, temperature and pressure may be recorded wirelessly, a feature that simplifies and facilitates surgical implantation and monitoring.

Some embodiments disclosed herein provide for real-time detection of seizures. Increases in temperature and pressure may occur shortly before or at seizure onset. The detection of electrical signals for detecting seizures has been demonstrated. The tri-modal sensor 110's sensitivity and multi-modality capabilities allow detection of changes in one or more of temperature, pressure, and electrical activity at a single location for detecting seizures.

Some embodiments disclosed herein provide for assessment of efficacy of seizure therapy. Changes in temperature and pressure may be used to quantify seizure severity and frequency, using embodiments disclosed herein.

Using embodiments disclosed herein, various measurements and assessments may be made, including but not limited to the following: assessment of motor, sensory, visual and cognitive functions (signal input to, processing by, and output from brain regions is associated with increases in local temperature); measurement of blood perfusion to brain; brain (parenchymal) pressure; CSF pressure measurement; intracranial blood pressure measurements from which pulse rate and arterial blood measurements may be also derived (sensor's temporal resolution allows this with use of analog or digital filters); respiratory rate measurements from brain (via filtered sensor's raw output); heart rate from brain data; prolonged/continuous systemic blood pressure measurements from a peripheral artery; and/or prolonged/continuous body/organ temperature measurements.

Some embodiments herein may utilize a Surface Acoustic Wave (SAW) sensor as a temperature sensor. In one embodiment, the SAW sensor may also be used in a modified configuration (as compared to its use as a temperature sensor) to measure pressure. In one embodiment, a sensitivity of 5 mbar (2 in. $H_2O$; 0.0725 psi) may be achieved using the SAW sensor as a pressure sensor. In one embodiment, the tri-modal sensor provides for measuring simultaneously temperature, pressure, and electrical activity, which provides for a tri-modality sensor for brain function monitoring from the same location at the same time.

Figure 2A:
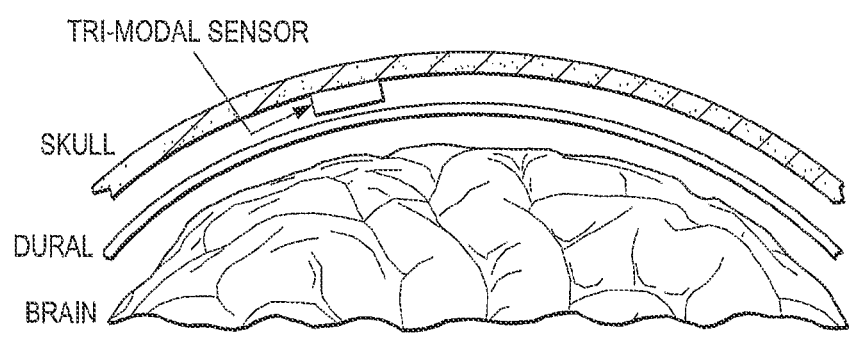
FIG. 2A shows a stylized representation of a placement of a tri-modal sensor, in accordance with one embodiment of the present disclosure.
Figure 2B:
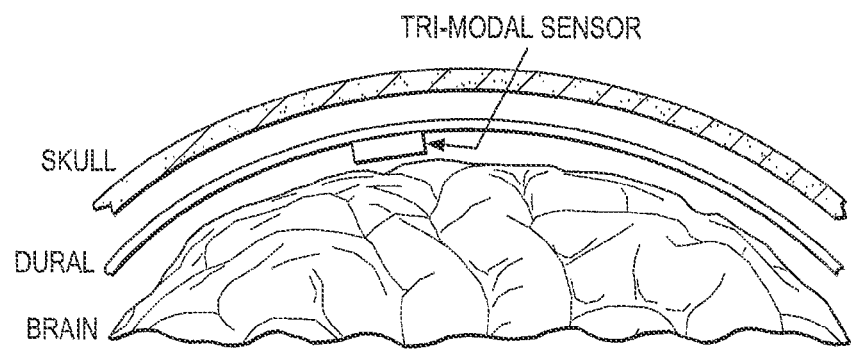
FIG. 2B shows a stylized representation of an alternative placement of a tri-modal sensor, in accordance with another embodiment of the present disclosure.

Turning now to FIGS. 2A and 2B, stylized representations of placements of the tri-modal sensor in a patient's head region, in accordance with some embodiments, are illustrated. More particularly, the tri-modal sensor 110 may be placed within the skull of a patient. In one embodiment, the tri-modal sensor 110 may be affixed to the inner surface of the skull, above the dura, as exemplified in FIG. 2A. In an alternative embodiment, tri-modal sensor 110 may be affixed inside the dura, as exemplified in FIG. 2B. In yet other embodiments (not shown), the tri-modal sensor 110 may be affixed within the brain parenchyma, within a brain ventricle, on the outer surface of a cerebral artery, or near the venous sinuses. More generally, the tri-modal sensor 110 may be placed in various regions proximate to the brain and remain within the spirit and scope of various embodiments of the present disclosure.

In other embodiments, the tri-modal sensor 110 may be placed in other organs or areas of a patient's body. For example, the tri-modal sensor 110 may be placed at a region of the patient's chest (e.g., near the heart's point of maximal impulse); an artery or venous structure; near a bone structure; in or within/adjacent to a muscle; in or near an eye region; or subdermally Careful selection of the site of deployment may allow the tri-modal sensor 110 to be used to sense (as one or more of an electrical, pressure, or temperature signal modality) a variety body signals such a heart rate, blood pressure, breathing rate or pattern, temperature, muscle force, etc.

Turning now to FIGS. 3A and 3B, stylized representations of the tri-modal sensor, in accordance with some embodiments, are illustrated. FIG. 3A illustrates a tri-modal sensor housing 310 for the tri-modal sensor 110. The housing 310 comprises an inner chamber within which an electrical sensor element 320, a temperature sensor element 330, and a pressure sensor element 340 may be located. The housing 310 may also comprise one or more wires/leads 312 capable of providing communications between one or more of elements 320, 330, and 340 with a medical device (e.g., IMD 120). In one embodiment, wire 312 may also provide power to the sensor elements 320, 330 and/or 340. Housing 310 may also comprise a power interface 345 capable of receiving power from one or more external sources, e.g., via inductive coupling, capacitive coupling, radio frequency (RF) coupling, microwave coupling, etc.

Housing 310 may also include a controller 370 configured to control the operation of the sensors 320, 330, 340 and the power interface 345. The controller 370 may comprise programmable control circuitry, a processor, a communications unit, signal filters, amplifiers, digital signal processors, analog-to-digital converters, memory, and/or the like. The tri-modal sensor 110 of FIG. 3 may provide for substantially simultaneous recording and/or transmitting of one or more of temperature, pressure and electrical activity from the same locus or body site.

Referring to FIG. 3B, a housing 350 comprises components similar to those found in the housing 310 of FIG. 3A. However, instead of a wire/lead 312 of FIG. 3A, the tri-modal sensor housing 350 of FIG. 3B comprises a wireless interface 355. The wireless interface 355 provides for communications between the tri-modal sensor housing 350 and a medical device (e.g., the IMD 120 and/or the EMD 130). The wireless interface 355 may comprise an antenna and/or other circuitry configured to allow for wireless data and/or power communications between the tri-modal sensor housing 350 and another medical device.

Turning now to FIGS. 3C and 3D, stylized representations of the tri-modal sensor, in accordance with alternative embodiments, are illustrated. FIG. 3C illustrates a tri-modal sensor housing 360 for the tri-modal sensor 110. The housing 360 comprises an inner chamber within which a plurality of electrical sensors 362, 364, temperature sensors 372, 374, and pressure sensors 382, 384 may be located. FIG. 3C illustrates the housing 360 having a matrix of sensors in an exemplary 3×2 matrix. However, those skilled in the art having benefit of the present disclosure would appreciate that any size matrix may be implemented, i.e., an "n×m" matrix (wherein n, m are integers). The matrix in the housing 360 may be arranged to activate and acquire body signals simultaneously or serially (e.g., multiplexing), in various predetermined patterns or on command.

The housing 360 may also comprise a wire/lead 312 capable of providing communications with a medical device (e.g., IMD 120, EMD 130). The housing 360 may also comprise a power interface 386 capable of receiving power from an external source, e.g., via inductive coupling, capacitive coupling, radio frequency (RF) coupling, microwave coupling, etc. The housing 360 may also include a controller 370 configured to control the operation of the sensor matrix and the power interface 386. FIG. 3D illustrates a device similar to the device of FIG. 3C, except that the housing 390 of FIG. 3D comprises a wireless interface 395 instead of a lead 312. The wireless interface 395 may comprise an antenna and/or other circuitry configured to allow for wireless communications with the tri-modal sensor housing 390.

Turning now to FIGS. 4A and 4B, a stylized diagram of a tri-modal sensor, in accordance with some embodiments is illustrated. FIG. 4B illustrates a cross-section of the tri-modal sensor of FIG. 4A. FIG. 4A illustrates a tri-modal sensor 410 comprising a pressure sensor 420, a temperature sensor 430 and electrical sensors (e.g., electrodes) 450, 470. The tri-modal sensor 410 is illustrated as have a cylindrical structure. However, a variety of types, dimensions and shapes of housing for the tri-modal sensor 410 may be utilized and remain within the spirit and scope of embodiments herein.

As illustrated in greater detail in FIG. 4B, the tri-modal sensor 410 comprises at least three regions, a quartz substrate region 460 for the pressure sensor 420, an inert gas region 440 at a reference pressure, and a $LiNbO_3$ substrate 432 for the temperature sensor 430. The pressure sensor 420 and the temperature sensor 430, in one embodiment, may be SAW sensors. However, the pressure sensor 420 and the temperature sensor 430 may be implemented using other types of sensor elements that detect pressure and/or temperature changes.

In one embodiment, a SAW sensor 430 adjacent to a $LiNbO_3$ substrate 432, which is sensitive to temperature but substantially insensitive to pressure, may be used as part of the rigid bottom cylindrical wall to sense temperature. Conversely, at the top of tri-modal sensor 410, a relatively thin diaphragm 425 may be attached. In one embodiment, the entire housing is sealed with inert gas such as nitrogen at a reference pressure. As the diaphragm deflects due to a change in pressure $\delta p$, the quartz substrate 460 bends proportionally, causing elongation or contraction of the SAW substrate along its length. Correspondingly, the travel time of sound changes in the SAW sensor as a linear function of pressure for deflections that are small relative to the length of the diaphragm, thereby allowing for measurement of pressure in sensor 420.

Figure 4C:
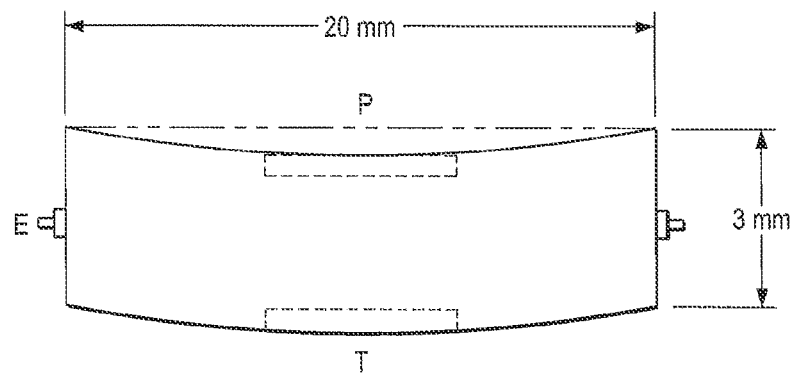
FIG. 4C shows a stylized diagram of a tri-modal sensor in accordance with an embodiment of the present disclosure.
Figure 4D:
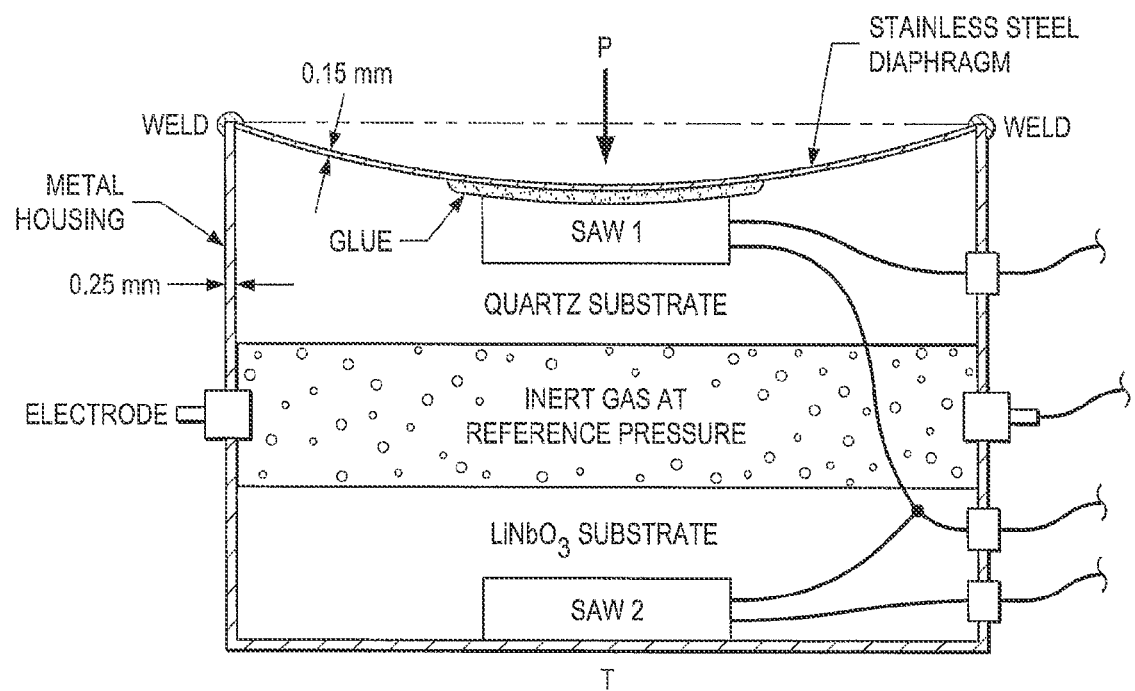
FIG. 4D shows a stylized cross-sectional representation of a tri-modal sensor of FIG. 4D in accordance with one embodiment of the present disclosure.

Referring to FIG. 4C below, an exemplary tri-modal sensor in the configuration of a semi-circular cylinder housing with overall dimension of 20 mm length and 3 mm diameter, in accordance with one embodiment, is illustrated. In the example of FIG. 4C, two SAW sensors of dimensions 5 mm×2 mm×0.5 mm may be housed inside (in part or in whole) a cylindrical housing to measure temperature and pressure. The housing may be fabricated of metal in some embodiments, and may itself may be used as an electrode for sensing or stimulating neuronal tissue. As showing in FIG. 4C, a SAW sensor with a $LiNbO_3$ (lithium niobate) piezoelectric substrate that is highly sensitive to temperature changes but substantially insensitive to pressure changes may be used as part of the rigid bottom cylindrical wall. On top of the semi-circular cylinder of FIG. 4C, a thin diaphragm may be attached. A quartz piezoelectric substrate, which is not sensitive to temperature changes, may be attached underneath the diaphragm for sensing pressure. The entire housing may be sealed with inert gas such as $N_2$ in the chamber at a reference pressure. As the diaphragm deflects due to a change in pressure $\delta p$, the quartz substrate bends commensurately with it, causing elongation or contraction of the SAW substrate along its length. Correspondingly, the travel time of sound changes in the SAW sensor as a linear function of pressure changes caused by diaphragm deflections that are small relative to the length of the diaphragm, thereby allowing for reliable measurement of pressure changes.

In one embodiment, only certain parts of the cylindrical enclosure are metal, and such metal parts may be arranged in a certain geometrical pattern to map electrical fields. While a cylindrical shape may be the preferred shape, any other shape (or dimensions) may be used according to the clinical application, the body organ/part being monitored and the organ site under monitoring.

Figure 5:
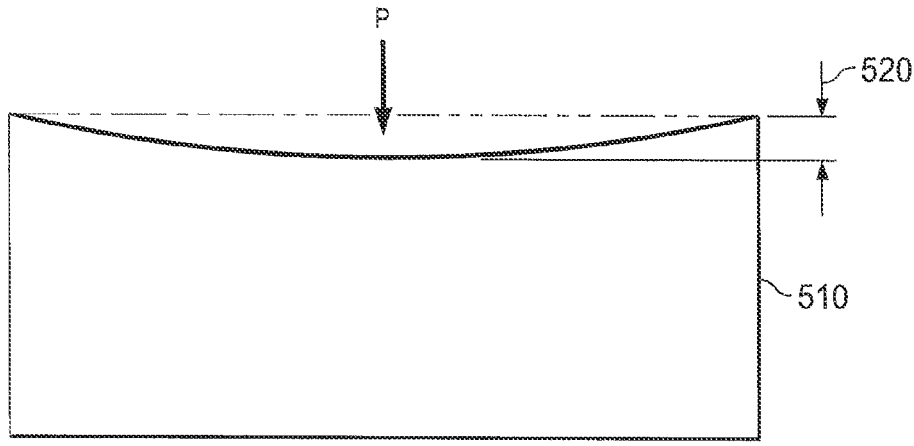
FIG. 5 shows a stylized depiction of the deflection of a diaphragm of an exemplary pressure sensor, in accordance with some embodiments of the present disclosure.

In one embodiment, the SAW sensor provides for a generally indirect measurement; that is, a thin diaphragm may be used as a primary sensor to convert pressure into bending or deflection. When the SAW substrate (quartz) itself is used as a diaphragm, the bending results in elongation of the substrate which in turn changes the travel time of sound. Embodiments herein provide for utilizing this concept for brain intra-cranial or intra-cerebral pressure measurement. Intracranial or intracerebral pressure measurements yield indirect information about global, regional or local brain function. The tri-modal sensor 110 may be manufactured to fit a variety of profiles for implanting into brain or into other organs or body parts. For example, a circular cylinder with a membrane welded on the top (as shown in FIG. 5 below), may be employed in some embodiments herein.

The pressure-sensitive membrane has the dimensions of diameter d and thickness t. The membrane deflection s is a function of differential pressure δp, its dimensions (d and t), and its material constants (elastic modulus E and Poisson's ratio, μ). For s/d small, s is a linearly related to pressure δp:

$$s \approx \frac{\partial p (d/2)^4}{Et^3} \cdot \frac{3(1-\mu^2)}{16} = \gamma \partial p \qquad (1)$$

The relative elongation is:

$$\partial L \approx 2s \qquad (2)$$

The change of the sound delay time is:

$$\Delta \tau \approx 2\gamma \partial p/c, \qquad (3)$$

Where c is the velocity of sound. The corresponding phase shift for the SAW delay line with resonance frequency, f, is:

$$\Delta \phi = 2 \cdot \gamma \cdot f \cdot 360° \cdot \partial p/c = S_{\partial p}^{\Delta \phi} \cdot \partial p \qquad (4)$$

The sensitivity parameter, $$S_{\partial p}^{\Delta \varphi} = \frac{\partial \varphi}{\partial p}, \qquad (5)$$

is related to the response of the SAW sensor and can be measured directly.

In some embodiments, three variants of a SAW pressure sensor may be provided. In one embodiment, the tri-modal sensor may be fabricated in the form of a semicircular cylinder with length 20 mm and diameter 3 mm (FIG. 6B below) with the housing wall thickness of 0.25 mm (stainless steel strip) and membrane thickness t=0.25 mm, 0.2 mm and 0.15 mm. Based on Equation (1) above, one maximal sensitivity may be for the thinnest membrane t=0.15 mm. In one embodiment, in light of the relative lack of cross sensitivity to temperature changes, a quartz sensor for pressure measurement may be utilized. Alternatively, a LiNbO₃ sensor, which may be used for temperature sensing, may also be used for pressure sensing. In one embodiment, the resonance frequency of the sensor may be approximately f=434 MHz, and its time delay may be τ=(1±0.1) μs.

In one embodiment, the lithium niobate crystal may be adhered (e.g., by glue) to the inside of the membrane wall. The membrane may then be joined to the housing by laser welding. In one embodiment, the sizes of LiNbO₃ substrate are 5×2×0.5 mm. In one embodiment, the membrane deflection for a pressure of 0.4 [atm] may be approximately 20 μm, while the deflection for the substrate may be approximately 10 μm.

Figure 6A:
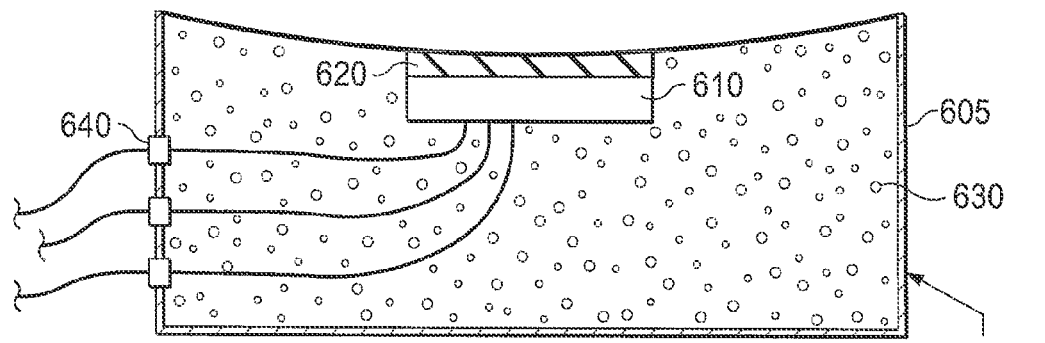
FIG. 6A shows a stylized depiction of one embodiment of the fabricated pressure sensor of FIG. 5.
Figure 6B:
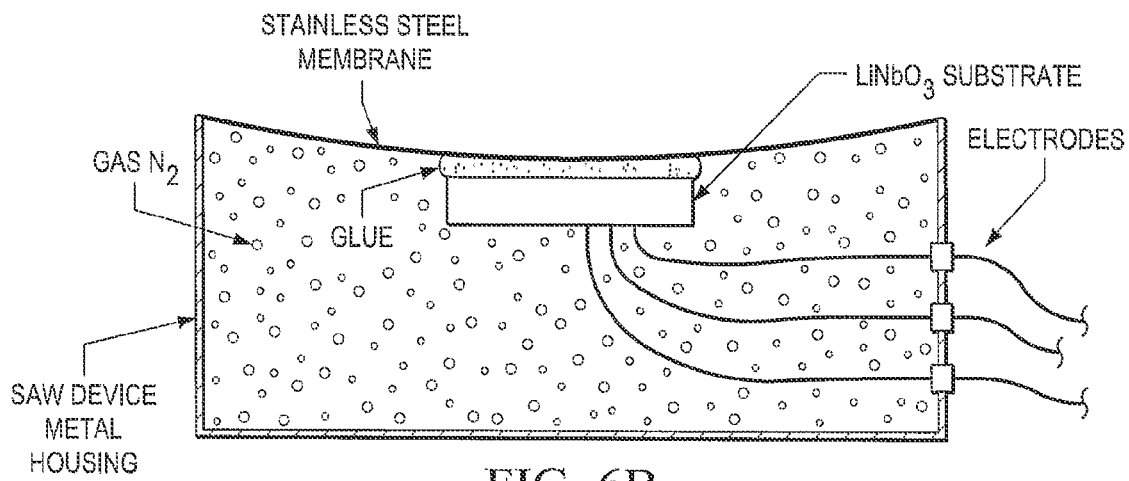
FIG. 6B shows a schematic diagram a fabricated pressure sensor with its housing, in accordance with one embodiment.
Figure 6C:
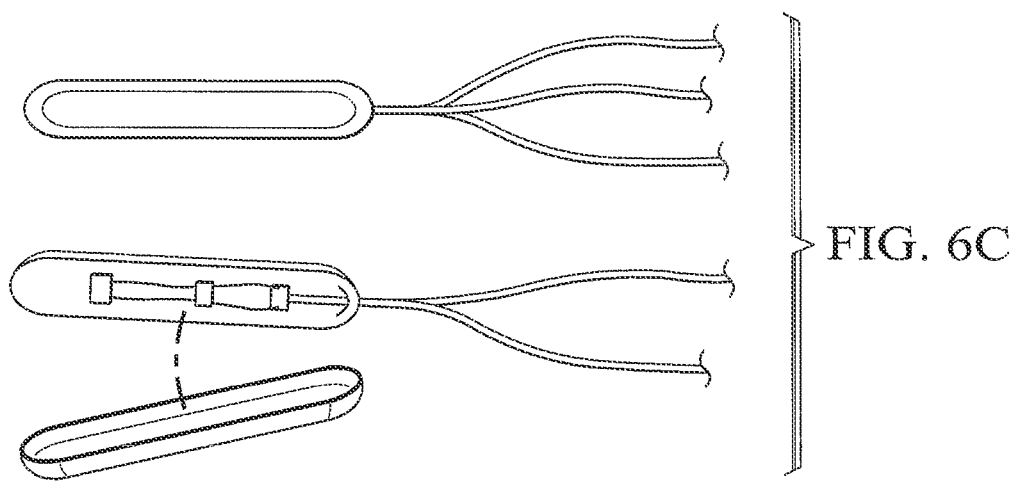
FIG. 6C shows a close-up view of the fabricated pressure sensor and housing of FIG. 6B, in accordance with one embodiment.
Figure 6D:
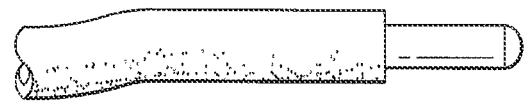
FIG. 6D provides an illustration of a temperature sensor, in accordance with one embodiment of the present disclosure.

FIGS. 6B and 6C provide a schematic diagram and a close-up view of the fabricated pressure sensor with its housing, in accordance with one embodiment. FIG. 6D provides an illustration of a temperature sensor, in accordance with one embodiment.

Figure 13:
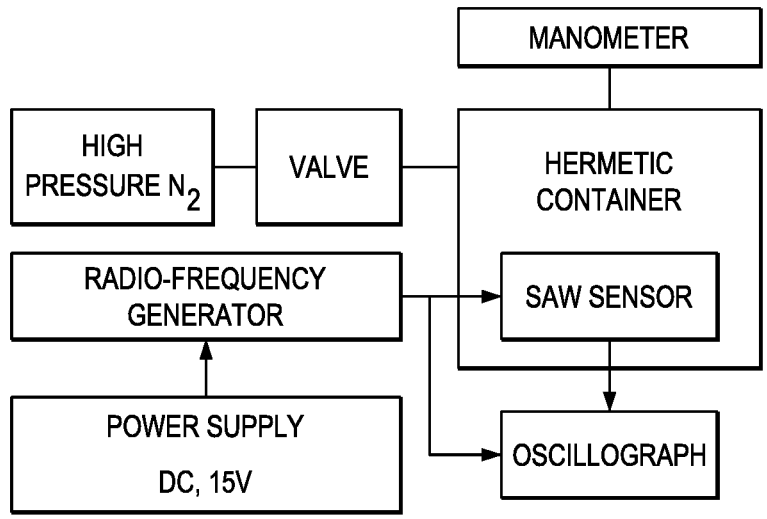
FIG. 13 shows a schematic diagram of an exemplary setup for testing an operation of a pressure SAW sensor suitable for incorporation into some embodiments of the present invention, are illustrated. In one embodiment, the SAW sensor may be excited with an oscillator at a resonant frequency $f_R=434$ MHz, and the SAW output signal may be measured using an oscilloscope.
Figure 14:
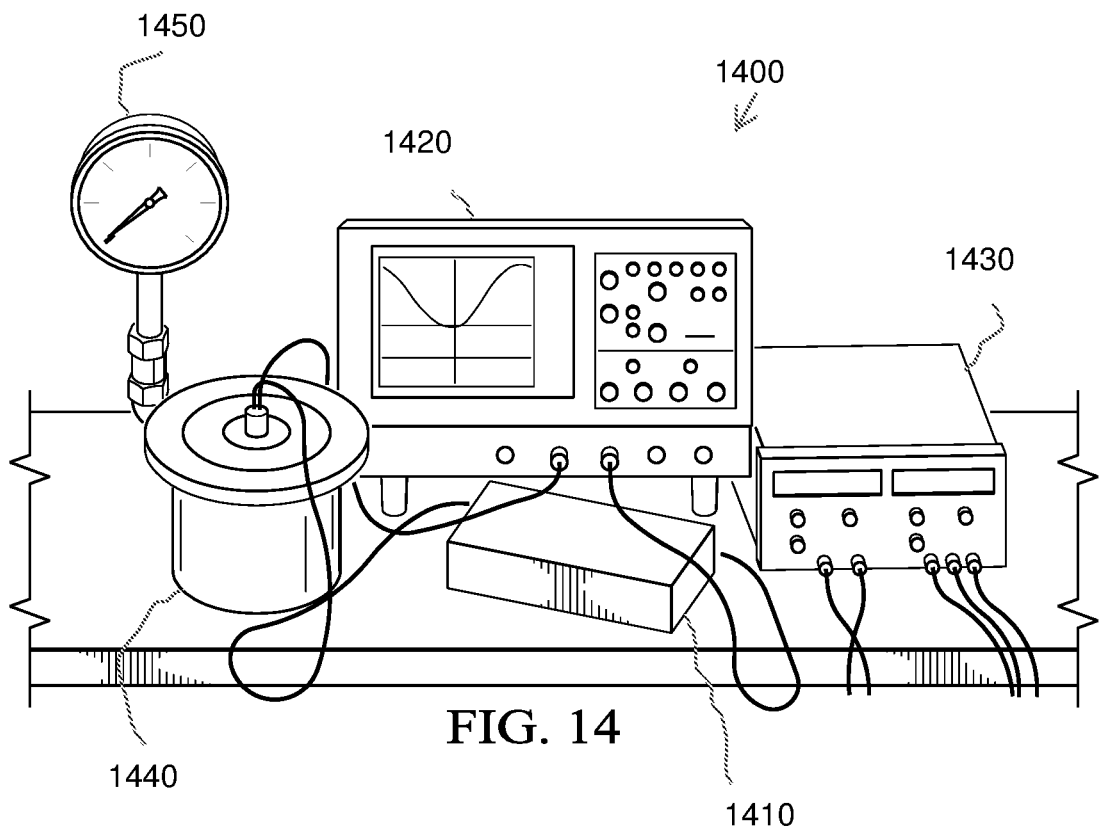
FIG. 14 shows a photograph of an exemplary test setup used for testing a pressure SAW sensor suitable for incorporation into some embodiments of the present invention.
Figure 15:
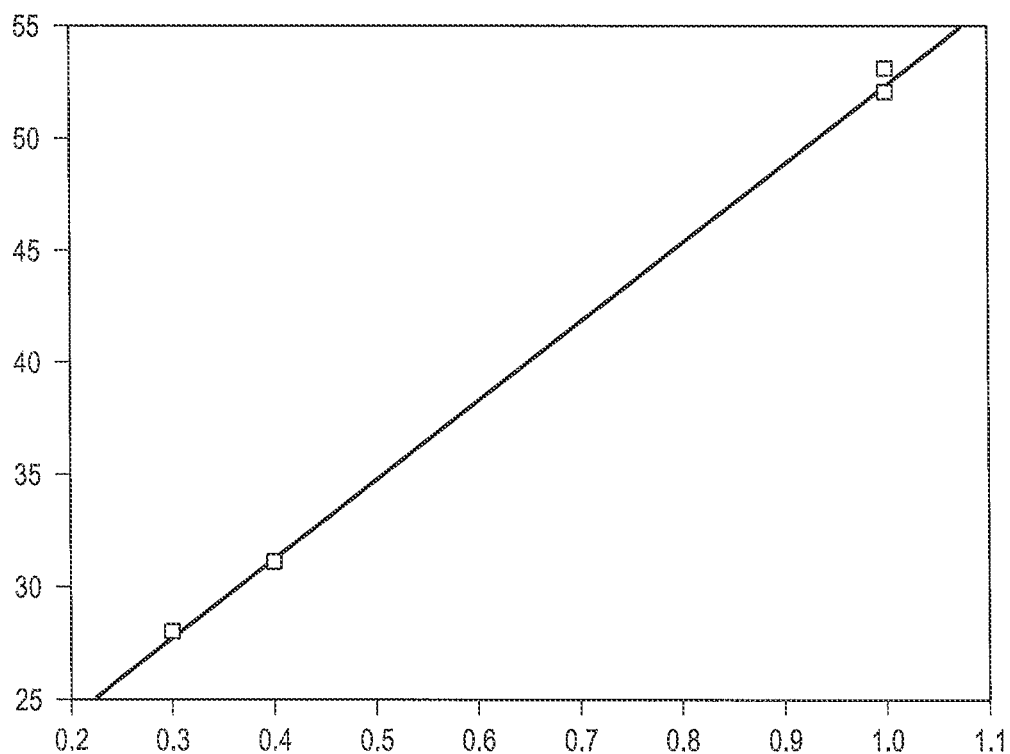
FIG. 15 shows a graph of the phase shift of a SAW sensor with differential (excess) pressure, according to Table 1, infra.

Turning now to FIGS. 13 and 14, an exemplary setup 1400 for testing an operation of a pressure SAW sensor, in accordance with one embodiment, are illustrated. In one embodiment, the SAW sensor may be excited with an oscillator 1410 at a resonant frequency $f_R$=434 MHz, and the SAW output signal may be measured using an oscilloscope 1420. The amplitude of the input sinusoidal signal on the SAW sensor may be a constant signal, approximately 280 mV. In one embodiment, the resultant output of the amplitude on the SAW sensor may be approximately 30 mV. (Power for the system may be provided by a 15V DC power supply, e.g., 1430). In one embodiment, the pressure sensor may be housed in a vacuum tight chamber 1440. In one embodiment, the chamber may be pressurized to a desired test pressure by introducing nitrogen. A standard manometer 1450 with a resolution of ±0.1 bar may be used to measure the pressure in the chamber. A plot of the phase shift of the SAW sensor with differential (excess) pressure is exemplified in Table 1 and in FIG. 15, in accordance with one embodiment.

TABLE 1

Measured values of the pressure SAW sensor characteristic.

| ΔP, Bar | Δφ, phase degrees |
|---|---|
| 0.3 | 28 |
| 0.4 | 31 |
| 1 | 52 |
| 1 | 53 |

In one embodiment, the SAW sensor sensitivity may be given by:

$$S_P^{\Delta \varphi} = \frac{\Delta \varphi}{\Delta p} \approx 36 \text{ phase degree/bar}$$

In one embodiment, the sensors provide for a minimal phase change registration of $\Delta \phi_{min}$~0.2 degree. Therefore, the developed pressure SAW sensor may register a pressure change provided by:

$$(\Delta p)_{min} \geq \frac{(\Delta \varphi)_{min}}{S_P^{\Delta \varphi}} \approx 5 \cdot 10^{-3} \text{bar}.$$

Referring to FIG. 5, a stylized depiction of the deflection of the diaphragm 425 is illustrated. The pressure sensor portion 510 comprises a diaphragm that may be deflected by changes in pressure. The amount of deflection 520 is proportional to the differential pressure (see Equation (1) above).

FIG. 6A illustrates a stylized depiction of one embodiment of a fabricated pressure sensor 605. The housing of the pressure sensor 605 may be filled and sealed with a gas 630, e.g., nitrogen or helium. The sensor 605 comprises a quartz substrate 610, underneath a dielectric material 620. In one embodiment, the housing may be made of a metal. Electrodes from the quartz substrate 610 are connected to the housing, for connection to the interface of the tri-modal sensor 410. The tri-modal sensor 410 and components thereof illustrated in FIGS. 4A-6 provide for acquiring substantially simultaneous pressure, temperature, and electrical body signals from designated target locations of a patient body.

Turning now to FIG. 7, a stylized depiction of a medical device capable of interfacing with a tri-modal sensor, in accordance with some embodiments, is illustrated. The medical device 700 of FIG. 7 may be an implantable medical device, or alternatively, an external medical device. The medical device 700 is capable of communicating with the tri-modal sensor 110.

Various components of the medical device 700, such as controller 710, processor 715, memory 717, power supply 730, communication unit 740, warning unit 792, therapy unit 794, logging unit 796, have been described in other patent applications assigned to Flint Hills Scientific, L.L.C. or Cyberonics, Inc., such as those incorporated by reference, supra. The medical device 700 may comprise a body data module 755 configured to receive various body data signal from the patient's body. For example, the body data module 755 may receive autonomic data, neurologic data (including kinetic data, cognitive data, EEG/ECoG data, evoked responses, etc.), endocrine data, metabolic data, tissue stress marker data, physical fitness data, and/or the like. In one embodiment, the body data module 755 processes signals provided by the tri-modal sensor 110. More information regarding multiple body data types, data collection thereof, and use thereof in epileptic event detection may be found in other patent applications assigned to Flint Hills Scientific, L. L. C. or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference. In one embodiment, the body data module 755 is capable of performing analysis of the body data, wherein the analysis may include look up functions, comparison function, and/or other processing function from which one or more conclusions regarding the patient's health (seizure detection, patient health evaluation, etc.) may be performed.

The medical device 700 may comprise one or more additional modules such as a warning unit 792 configured to issue a warning of the onset of a seizure, a therapy unit 794 configured to deliver a therapy in response to a detection of an onset of a seizure, a severity unit 798 configured to determine a seizure severity index, or a logging unit 796 configured to log at least one of a date and time of occurrence of the seizure, a type of seizure, a seizure severity index, a time of and type of therapy in response to a seizure detection, or an effect of a therapy provided in response to a seizure detection.

The medical device 700 comprises a tri-modal sensor interface 770 that is capable of interfacing with a tri-modal sensor 110. A more detailed description of the tri-modal sensor interface 770 is provided in FIG. 8 and accompanying description below. The tri-modal sensor interface 770 may provide data to the pressure data unit 772, temperature data unit 774 and the electrical data unit 776. These data units may provide the tri-modal data to other portions of the medical device 700 for detecting a seizure and/or perform a responsive action (e.g., provide a warning, administer a therapy, log data regarding a pathological event, etc.). In an alternative embodiment, the units 772, 774, 776 may be a part of the body data module 755.

In some embodiments, the medical device 700 may also comprise a functional mapping unit 750. The functional mapping unit 750 may correlate body data from the tri-modal sensor 110 to a patient's activity. In one embodiment, the body data from the tri-modal sensor may be correlated to one or more of a type or level of activity such as motor (e.g., movement of a body part such as a finger), sensory including all special senses (e.g., feeling touch or cold in a certain part of the body) or cognitive (e.g., speaking, comprehending spoken language, etc.) to localize their anatomo-functional representation in the brain to generate functional brain maps. The functional mapping data may create a map of the brain, correlating patient activities as well as body data provided by the tri-modal sensor 110 to one or more regions of the patient's brain. A more detailed illustration of the functional mapping unit 750 is provided in FIG. 11, and accompanying description below.

Figure 8:
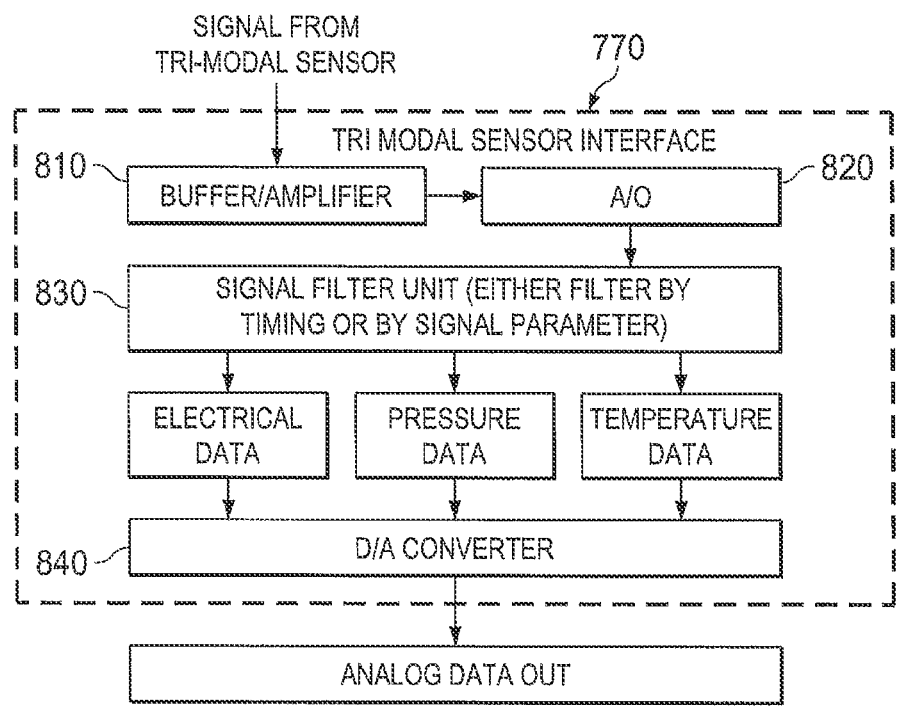
FIG. 8, shows a stylized block diagram depiction of a tri-modal sensor interface of FIG. 7, in accordance with some embodiments.

Turning now to FIG. 8, a block diagram depiction of the tri-modal sensor interface 770 of FIG. 7, in accordance with some embodiments of the present disclosure, is illustrated. The tri-modal sensor interface 770 may comprise a buffer/amplifier 810, an analog to digital converter (A/D converter) 820, and a signal filter unit 830. The buffer/amplifier 810 may comprise a buffer amp for buffering the signals from the tri-modal sensor 110. In one embodiment, three different buffer/amplifiers may be present, one for the pressure signal, a second for the temperature signal, and a third for the electrical signal from the tri-modal sensor 110. In one embodiment, each of the buffer/amplifiers may comprise circuitry that handles specific signal characteristics of each of the pressure, temperature, and electrical signals from the corresponding sensing elements of the tri-modal sensor.

The output from the buffer/amplifier 810 may be provided to the A/D converter 820. The A/D converter 820 may also comprise three unique portions, each with its own analog to digital converter. Each portion of the A/D converter 820 may contain separate circuitry to handle specific signal characteristics of each of the pressure, temperature, and electric signals, respectively. The A/D converter 820 may provide digitized pressure data, temperature data, and/or electrical data to the signal filter unit 830.

The signal filter unit 830 may comprise one or more filters and/or digital signal processors (DSPs). The signal filter unit 830 may comprise three portions wherein each portion handles specific signal characteristics of each of the pressure, temperature, and electric signals, respectively. The filtering performed by the signal filter unit 830 may include noise filtering, correlation, stacking, etc. The signal filter unit 830 may filter by timing characteristics and/or by signal parameters/characteristics. The signal filter unit 830 provides output of electrical data, pressure data, and temperature data associated with the patient's body. In one embodiment, the tri-modal sensor interface 770 may also comprise a digital to analog converter (D/A converter) 840. The D/A converter 840 may contain separate circuitry sub-units each of which handles specific signal characteristics of each of the pressure, temperature, and electric signals, respectively. The D/A converter 840 may convert digital signals from the signal filter unit 830 to analog signal and provide analog data out, which may include analog pressure, temperature, and/or electrical data.

Figure 9A:
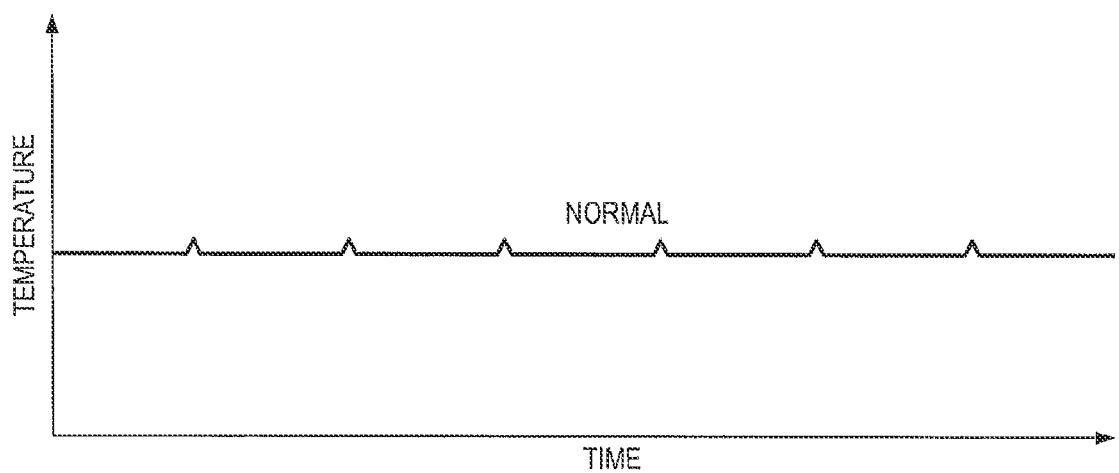
FIGS. 9A and 9B show exemplary diagrams of a temperature signal acquired by a tri-modal sensor, in accordance with some embodiments of the present disclosure.
Figure 9B:
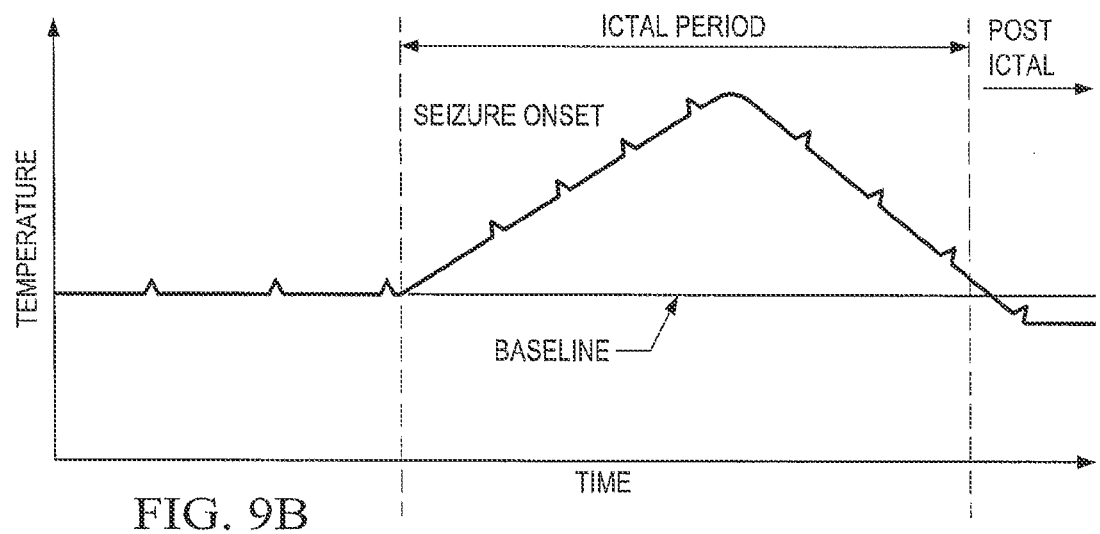

Turning now FIGS. 9A and 9B, an exemplary diagram of a temperature signal acquired by the tri-modal sensor 110, in accordance with some embodiments, is illustrated. For example, at a 5 Hz sampling rate, a temperature signal for a normal (non-seizure) time period is illustrated in FIG. 9A.

Alternatively, the temperature reading may be a DC value reading. FIG. 9A shows that the temperature is fairly stable for a patient in a normal state. In contrast, at the onset of a seizure, the temperature may rise in a steady manner (see FIG. 9B) to a peak during an ictal period. FIG. 9B also indicates a steady decline in temperature beginning in the ictal time period. Depending upon the nature of the seizure, the decline in temperature may begin at a post-ictal period (i.e., the temperature may not begin its decline from the peak temperature until the end of the seizure). At a post-ictal time period, the temperature reading from the tri-modal sensor 110 may indicate a return to baseline temperature, or even lower. In the case of absence seizures, the temperature reading from the tri-modal sensor 110 indicate a decline in temperature (from baseline) during the ictal period, and returning to approximately to baseline during the post-ictal time period. The change in temperature as detected by the tri-modal sensor 110 may be used separately, or in combination with other data from the tri-modal sensor 110 to perform seizure detection and treatment.

Figure 10A:
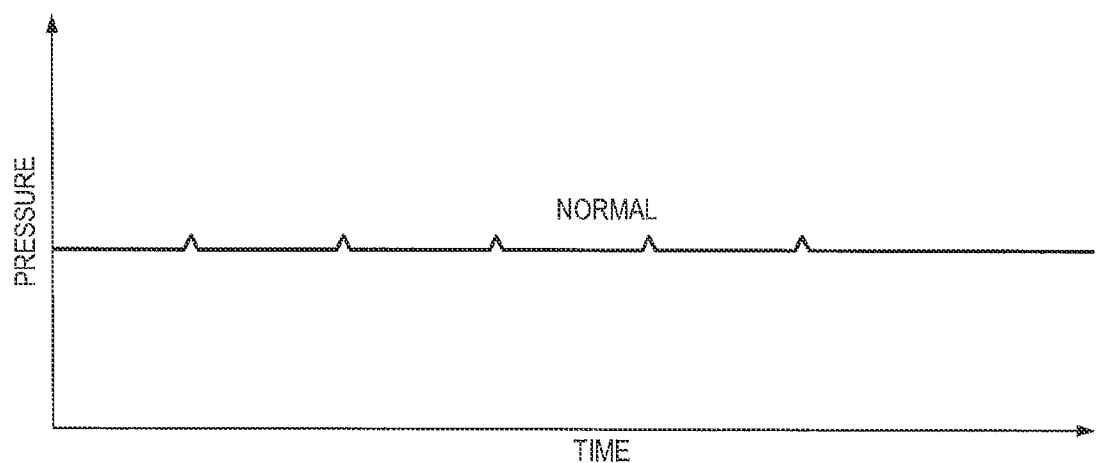
FIGS. 10A and 10B show exemplary diagrams of a pressure signal acquired by a tri-modal sensor, in accordance with some embodiments.
Figure 10B:
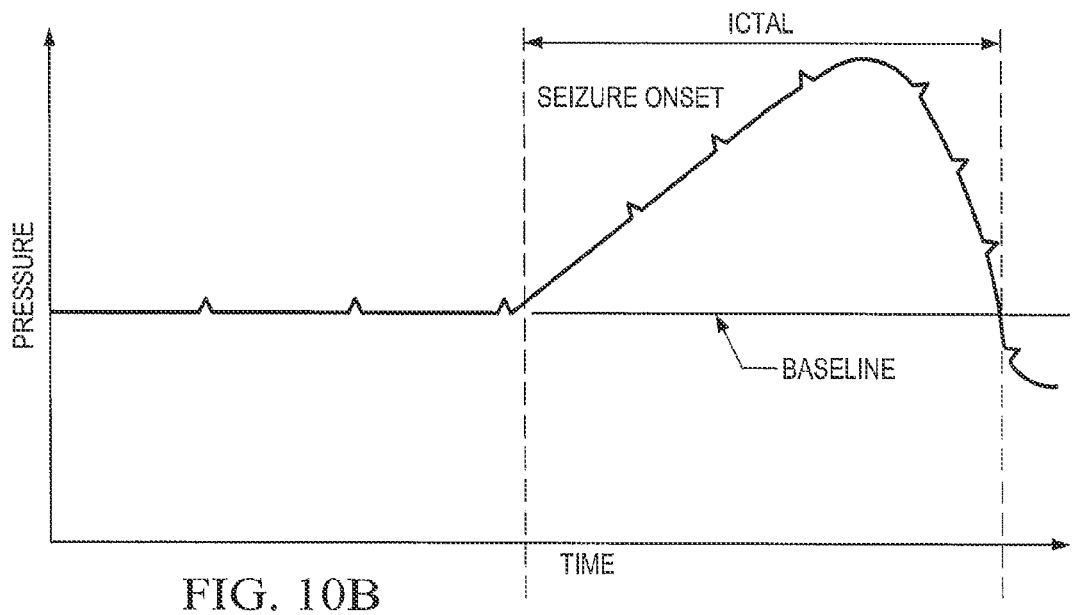

Turning now to FIGS. 10A and 10B, an exemplary diagram of a pressure signal acquired by the tri-modal sensor 110 in accordance with some embodiments is illustrated. The pressure signals may include, for example, intracranial pressures, intra-cerebral pressures, intra-ventricular pressures, spinal CSF pressures, or arterial blood pressures. FIG. 10A is an idealized example of intracranial or intra-cerebral pressure that is fairly stable for an epileptic patient in a non-ictal state. The body pressure signal may be sampled at a rate sufficient to identify transient changes on a timescale of interest, e.g., 10 Hz may be sufficient to identify desired features such as heart rate, although other sampling rates may be used as needed for a particular application. FIG. 10B depicts an increase in the intracranial or intra-cerebral pressure at the onset of the seizure, with a return to a baseline some time after the seizure ends. The change in pressure as detected by the tri-modal sensor 110 may be used separately, or in combination with other data from the tri-modal sensor 110 to perform seizure detection and treatment, in some embodiments.

Figure 11:
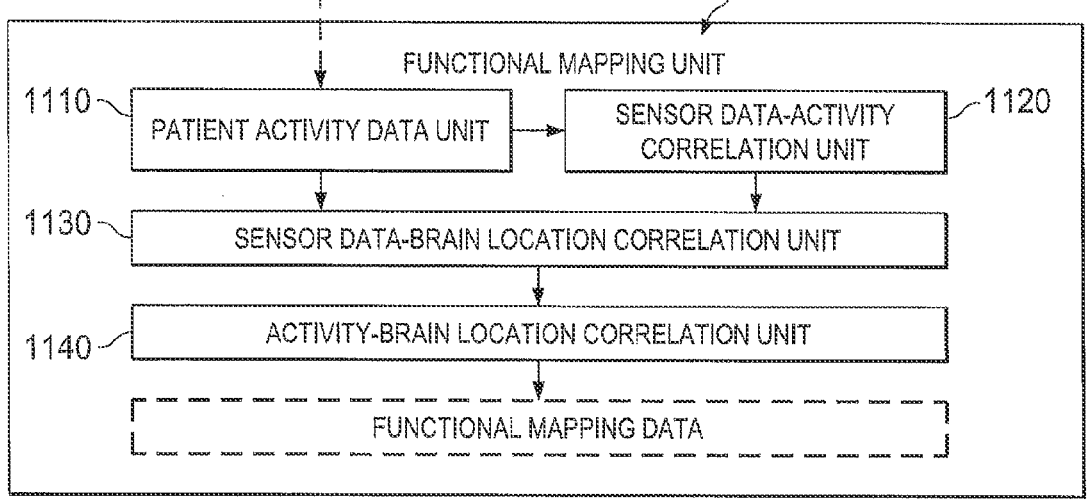
FIG. 11 shows a stylized block diagram depiction of a function mapping unit of FIG. 7, in accordance with some embodiments.

Turning now to FIG. 11, a stylized block diagram representation of a functional mapping unit 750 from FIG. 7 is illustrated, in accordance with some embodiments. The functional mapping unit 750 may comprise a patient activity data unit 1110, a sensor data-activity correlation unit 1120, a sensor data-brain location correlation unit 1130, and an activity-brain location correlation unit 1140. The patient activity data unit 1110 is capable of receiving information as to physical activities (e.g., resting, walking or jogging) of the patient. The unit 1110 may store a record of previous activity and timestamp such data. In one embodiment, the patient activity data unit 1110 is capable of providing messages or instructions to the patient, requesting the patient to perform certain activities, e.g., to sit down, to stand up, etc. The sensor data-activity correlation unit 1120 may perform a correlation between the data provided by the tri-modal sensor 110 and activities performed by patient. The unit 1120 may use time-stamping to assist in temporally correlating activities (e.g., strenuous, light activity, rest, etc.) to corresponding body data.

The sensor data-brain location correlation unit 1130 may receive data from the patient activity data unit 1110 and the sensor data-activity correlation unit 1120. The sensor data-brain location correlation unit 1130 is capable of mapping via temporal correlations sensor data related to motor, cognitive or other brain activities to neuronal activity at particular brain locations. Therefore, certain activities and certain body data may correlate to particular portions of the brain. The activity-brain location correlation unit 1140 is capable of correlating activity data, body data from the tri-modal sensor 110, and brain location data, in order to provide a brain functional map. The map may be created in real-time or using stored data.

Figure 12:
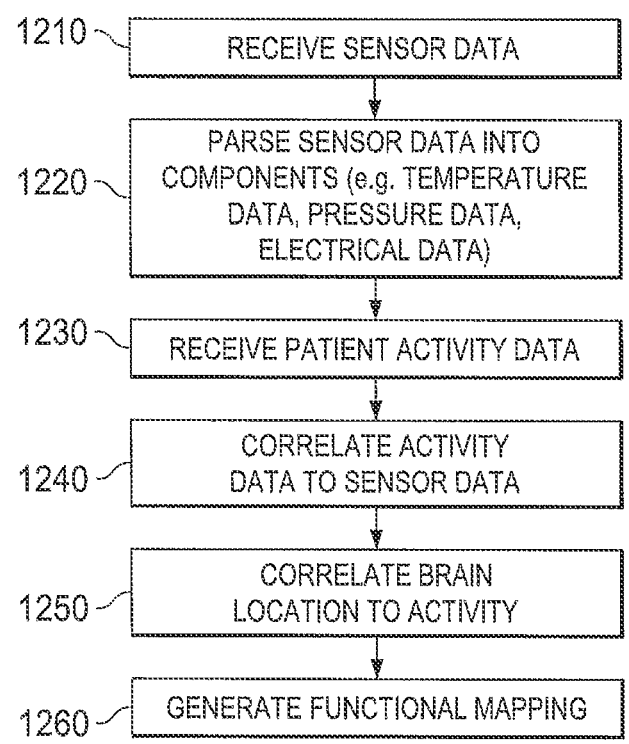
FIG. 12 show a stylized flowchart depiction of performing a functional mapping of a patient's brain, in accordance with some embodiments of the present disclosure.

Turning now to FIG. 12, a flowchart depiction of a method for performing a functional mapping of the brain, in accordance with some embodiments of the present disclosure, is provided. Sensor data is received by the medical device 700 (at 1210). The sensor data may include pressure data, temperature data, and/or electrical data from tri-modal sensor 110. The sensor data may be parsed into components, e.g., temperature data, pressure data, and electrical data. In one embodiment, the parsing of the data may be performed during the sensor data processing stage, or alternatively, after the raw sensor data is parsed (at 1220).

Patient activity data (e.g., body motion data indicative of physical activity or movement of the patient) is also received by the medical device 700 (at 1230). Patient activity data may be received directly (e.g., from patient input, etc.) or indirectly, by analyzing body data from, e.g., an accelerometer or inclinometer. Upon receiving activity data, a correlation between the activity data and the sensor data may be performed (at 1240). Further, the patient's activity may be correlated to one or more brain locations within the patient's brain (at 1250). This information may then be used to generate a functional mapping (at 1260) of the patient's brain. The functional mapping may be graphical e.g., graphs, diagrams, or numerical.

Utilizing embodiments herein, a more robust, in-depth and thorough analysis of the patient's body data may be performed in real-time. Acquiring pressure, temperature, and electric data from the same locus or from multiple loci on one or more of the patient's organs provides valuable clinical information about the patient's condition.

The methods depicted in FIG. 12 and/or described above may be governed by instructions that are stored in a non-transitory computer readable storage medium and that are executed by, e.g., a processor 717 of the medical device 700. Each of the operations shown in FIG. 12 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

What is claimed is:

1. An apparatus for sensing a body signal of a patient, comprising:
    an assembly capable of sensing a plurality of body signal types, wherein said body signal types comprise an electrical body signal, a temperature body signal, and a pressure body signal; said assembly comprising:
        an electrode configured to sense said electrical body signal;
        a first surface acoustic wave (SAW) sensor configured to sense said temperature body signal; and
        a second SAW sensor configured to sense said pressure body signal.

2. The apparatus of claim 1, wherein said assembly further comprises:
   a power interface for receiving electrical power and providing the electrical power to at least one component of said assembly.

3. The apparatus of claim 2, wherein said power interface is capable of receiving the electrical power based upon at least one of a wired coupling or a wireless coupling.

4. The apparatus of claim 3, wherein said wireless coupling of said power interface is at least one of an inductive coupling, a capacitive coupling, a radio frequency coupling or a microwave coupling.

5. The apparatus of claim 3, wherein said wireless coupling of said power interface is configured to provide at least one of an excitation function or an interrogation function for said apparatus.

6. The apparatus of claim 1, wherein said assembly further comprises a communication module, wherein said communication module comprises at least one of a wired or a wireless communication system, wherein said wireless communication system comprises an antenna operatively coupled to at least one of a transmitter or a receiver.

7. The apparatus of claim 1, wherein said assembly comprises an array of first SAW sensors, and an array of second SAW sensors.

8. The apparatus of claim 1, wherein said assembly comprises a diaphragm capable of proportionally deflecting in response to the pressure experienced by said diaphragm.

9. The apparatus of claim 1, wherein said assembly is configured to provide one or more signal indicative of the patient's blood pressure, pulse, and temperature within a predetermined period of time, and from a same location in the patient's body.

10. The apparatus of claim 1, wherein said assembly is configured to provide one or more signals indicative of a respiratory rate, a respiration amplitude, and a tidal volume from a patient's body.

11. The apparatus of claim 1, wherein said assembly is configured to provide one or more signals indicative of electrical activity, thermal activity and pressure within the patient brain.

12. The apparatus of claim 1, wherein said assembly further comprises a controller configured to control at least one operation of the assembly.

13. The apparatus of claim 1, wherein said assembly is adapted to being positioned at least one of:
   a region of the patient's brain;
   an artery;
   a subdural region;
   a brain ventricle;
   a muscle;
   an eye region; or
   sub-dermally.

14. The apparatus of claim 13, wherein said assembly is configured to detect epileptic seizures.

15. The apparatus of claim 13, wherein said assembly is configured to monitor intracranial pressure.

16. The apparatus of claim 13, wherein said assembly is configured to measure at least one of a temperature, a pulse, a blood pressure, force generated by muscles or ocular pressure.

17. The apparatus of claim 1, wherein said electrode is configured to deliver electrical stimulation.

18. The apparatus of claim 1, wherein said assembly is configured to be coupled to a catheter for delivering a medication.

19. The apparatus of claim 1, wherein said assembly is configured to be coupled to at least one of a treatment device, a warning device, or a logging device.

20. A medical device system, comprising:
   a probe comprising an electrical sensor capable of sensing an electrical body signal, a first surface acoustic wave (SAW) sensor capable of sensing a body temperature signal, and a second surface acoustic wave SAW sensor capable of sensing a body pressure signal; and
   a medical device capable of receiving said electrical body signal, said body temperature signal, and said body pressure signal from said probe.

21. The medical device system of claim 20, wherein said medical device further comprises:
   a controller for controlling one or more operations of said medical device;
   a communications interface capable of receiving data from said probe and transmitting data to said electrode;
   a tri-modal sensor interface capable of receiving body signals from said probe;
   a data processing unit to condition said body signals;
   a data analysis unit to perform an analysis of said body signals; and
   a functional mapping unit to perform a functional mapping of at least one brain activity, based on said analysis of said body signals.

22. The medical device of claim 20, wherein said function mapping unit comprises:
   a patient activity unit for at least one of detecting an activity of a patient, or providing a message to a patient relating to an activity;
   a sensor data-activity correlation unit to correlate data from said probe to an activity of said patient;
   a sensor data-brain location correlation unit to correlate data from said probe to a brain location of said patient; and
   an activity-brain location correlation unit to correlate activity of said patient to one or more brain locations, said activity-brain location correlation unit to provide functional mapping data for mapping a patient's brain.

23. A medical device, comprising:
   a probe capable of sensing a plurality of body signal types, wherein said body signal types comprise an electrical body signal, a temperature body signal, and a pressure body signal; said probe comprising:
      an electrode configured to sense said electrical body signal;
      a first surface acoustic wave (SAW) sensor configured to sense said temperature body signal; and
      a second SAW sensor configured to sense said pressure body signal; and
   a functional mapping unit to provide a functional mapping of a patient's brain.

* * * * *